US008021434B2

(12) United States Patent
Segura et al.

(10) Patent No.: US 8,021,434 B2
(45) Date of Patent: Sep. 20, 2011

(54) URETERAL STENT (75) Inventors: Joseph Segura, Rochester, MN (US); James Teague, Spencer, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1622 days.

(21) Appl. No.: 11/048,772

(22) Filed: Feb. 3, 2005

(65) Prior Publication Data
US 2005/0131547 A1 Jun. 16, 2005

Related U.S. Application Data (63) Continuation of application No. 10/093,040, filed on Mar. 7, 2002, now Pat. No. 6,913,625.

(51) Int. Cl.
*A61F 2/04* (2006.01)
(52) U.S. Cl. .................................... 623/23.7; 623/23.64
(58) Field of Classification Search ................ 623/23.7, 623/23.64–23.67, 26.64, 23.68, 23.72; 606/29–30; 604/8, 9
See application file for complete search history.

(56) References Cited

U.S. PATENT DOCUMENTS

| 2,644,376 | A | * | 7/1953 | Raymond | ............... | 493/296 |
|---|---|---|---|---|---|---|
| 3,783,454 | A | | 1/1974 | Sausse et al. | | |
| 3,938,529 | A | | 2/1976 | Gibbons | | |
| 3,995,642 | A | | 12/1976 | Adair | | |
| 4,212,304 | A | | 7/1980 | Finney | | |
| 4,225,979 | A | | 10/1980 | Rey et al. | | |
| 4,307,723 | A | | 12/1981 | Finney | | |
| 4,334,327 | A | | 6/1982 | Lyman et al. | | |
| 4,531,933 | A | | 7/1985 | Norton et al. | | |
| 4,551,137 | A | | 11/1985 | Osborne | | |
| 4,610,657 | A | | 9/1986 | Densow | | |
| 4,643,716 | A | | 2/1987 | Drach | | |
| 4,671,795 | A | | 6/1987 | Mulchin | | |
| 4,713,049 | A | | 12/1987 | Carter | | |
| 4,787,884 | A | | 11/1988 | Goldberg | | |
| 4,790,809 | A | | 12/1988 | Kuntz | | |
| 4,790,810 | A | | 12/1988 | Pugh, Jr. et al. | | |
| 4,790,816 | A | | 12/1988 | Sundblom et al. | | |

(Continued)

FOREIGN PATENT DOCUMENTS
EP 0808611 A3 12/1999
(Continued)

OTHER PUBLICATIONS

Hepperlen et al., "Self-Retained Internal Ureteral Stents: A New Approach," *The Journal of Urology*, Jun. 1978, vol. 119 (pp. 731-734).

(Continued)

*Primary Examiner* — Thomas J Sweet
*Assistant Examiner* — Christopher D Prone (57) ABSTRACT

A stent is designed to be placed within a patient's ureter to facilitate drainage from the patient's kidneys to the bladder. An elongated portion of the stent includes a length sufficient to extend substantially within the ureter from the kidney to the bladder, and defines a lumen extending therethrough. A first end portion extends from one end of the elongated portion and is adapted to assume a retaining configuration when placed substantially within the kidney. A second end portion extends from another end of the elongated portion and flares outward when placed substantially within the bladder to maintain position. The second end portion allows fluids to flow through the lumen and into the bladder and is collapsible to prevent fluid from passing from the bladder to the kidney.

20 Claims, 13 Drawing Sheets

U.S. PATENT DOCUMENTS

| | | | |
|---|---|---|---|
| 4,813,925 A | 3/1989 | Anderson, Jr. et al. | |
| 4,820,262 A | 4/1989 | Finney | |
| 4,874,360 A | 10/1989 | Goldberg et al. | |
| 4,913,683 A | 4/1990 | Gregory | |
| 4,931,037 A | 6/1990 | Wetterman | |
| 4,950,228 A | 8/1990 | Knapp, Jr. et al. | |
| 4,957,479 A | 9/1990 | Roemer | |
| 4,990,133 A | 2/1991 | Solazzo | |
| 4,990,228 A | 2/1991 | Perusich et al. | |
| 5,019,102 A | 5/1991 | Hoene | |
| 5,078,684 A | 1/1992 | Yasuda | |
| 5,116,309 A | 5/1992 | Coll | |
| 5,141,502 A | 8/1992 | Macaluso, Jr. | |
| 5,176,626 A | 1/1993 | Soehendra | |
| 5,221,253 A | 6/1993 | Coll | |
| 5,224,953 A | 7/1993 | Morgentaler | |
| 5,246,445 A | 9/1993 | Yachia et al. | |
| 5,269,802 A | 12/1993 | Garber | |
| 5,282,784 A | 2/1994 | Willard | |
| 5,346,467 A | 9/1994 | Coll | |
| 5,354,263 A | 10/1994 | Coll | |
| 5,356,432 A * | 10/1994 | Rutkow et al. | 623/23.72 |
| 5,364,340 A | 11/1994 | Coll | |
| 5,401,257 A | 3/1995 | Chevalier, Jr. et al. | |
| 5,514,176 A | 5/1996 | Bosley, Jr. | |
| 5,520,697 A | 5/1996 | Lindenberg et al. | |
| 5,531,741 A | 7/1996 | Barbacci | |
| 5,599,291 A * | 2/1997 | Balbierz et al. | 604/8 |
| 5,626,897 A * | 5/1997 | Goldstein | 426/139 |
| 5,647,843 A | 7/1997 | Mesrobian et al. | |
| 5,681,274 A | 10/1997 | Perkins et al. | |
| 5,684,051 A | 11/1997 | Thompson | |
| 5,782,916 A | 7/1998 | Pintauro et al. | |
| 5,795,319 A | 8/1998 | Ali | |
| 5,814,006 A | 9/1998 | Planz | |
| 5,921,952 A | 7/1999 | Desmond, III et al. | |
| 5,964,744 A | 10/1999 | Balbierz et al. | |
| 5,971,967 A | 10/1999 | Willard | |
| 5,984,965 A * | 11/1999 | Knapp et al. | 623/23.7 |
| 6,013,102 A | 1/2000 | Pintauro et al. | |
| 6,059,808 A | 5/2000 | Boussignac et al. | |
| 6,139,536 A | 10/2000 | Mikus et al. | |
| 6,165,200 A * | 12/2000 | Tsugita et al. | 606/200 |
| 6,616,685 B2 * | 9/2003 | Rousseau | 606/213 |
| 6,656,146 B1 * | 12/2003 | Clayman et al. | 604/8 |
| 6,764,519 B2 * | 7/2004 | Whitmore, III | 623/23.7 |
| 6,887,215 B2 * | 5/2005 | McWeeney | 604/9 |
| 6,913,625 B2 | 7/2005 | Segura et al. | |
| 2001/0053936 A1 | 12/2001 | Whitmore, III | |
| 2002/0032487 A1 * | 3/2002 | Dua et al. | 623/23.68 |

FOREIGN PATENT DOCUMENTS

| | | |
|---|---|---|
| WO | WO 97/17094 | 5/1997 |
| WO | WO 99/58083 | 5/1999 |
| WO | WO 00/66032 | 11/2000 |
| WO | WO 01/89415 | 11/2001 |
| WO | WO 01/91668 | 12/2001 |

OTHER PUBLICATIONS

Collier et al., "Proximal Stent Displacement as Complication of Pigtail Ureteral Stent," *Urology*, Apr. 1979, vol. XIII, No. 4 (pp. 372-375).

Mardis et al., "Polyethylene Double-Pigtail Ureteral Stents," *Urologic Clinics of North America*, Feb. 1982, vol. 9, No. 1 (pp. 95-101).

International Search Report for International Patent Application Ser. No. PCT/US03/05603, dated Jul. 8, 2003, 6 pages.

* cited by examiner

URETERAL STENT

This application is a continuation of application 10/093040, filed Mar. 7, 2002, now U.S. Pat. No. 6,913,625.

TECHNICAL FIELD

This invention relates to stents and methods of maintaining patency of a body lumen such as the ureter using stents.

BACKGROUND INFORMATION

A ureter is a tubular passageway in a body that conveys urine from the kidney to the bladder. Urine is transported through the ureter under the influence of hydrostatic pressure assisted by contractions of muscles located within the walls (lining) of the ureter. A urological condition that some patients experience is ureteral blockage or obstruction. Some common causes of such blockage are the formation of tumors or abnormalities within the ureteral lining or the formation and passage of kidney stones.

Ureteral stents are medical devices designed to extend through the ureter and to facilitate drainage from a kidney to the bladder when the ureter becomes blocked or obstructed. Generally, these stents are made from small diameter tubing of a biocompatible plastic. Ureteral stents may have multiple side holes to enhance drainage and typically include retention hooks or coils extending from both the kidney (distal) and bladder (proximal) ends of the tubing to prevent the migration of the ureteral stent after placement within the ureter.

SUMMARY OF THE INVENTION

The present invention generally relates to draining fluids from the kidney to the bladder of a patient with a stent. Devices and methods according to the invention are typically used in the treatment of patients suffering from an obstructed ureter to address and relieve urinary retention while minimizing patient discomfort. It is an object of the invention to maintain the ureter open and able to pass fluids from the kidney to the bladder. It is another object of the invention to minimize patient discomfort associated with a placed ureteral stent.

In one aspect, the invention relates to a ureteral stent. The ureteral stent includes an elongated portion, a first end portion extending from one end of the elongated portion, and a second end portion extending from another end of the elongated portion. The elongated portion has a length sufficient to extend substantially within the ureter from the kidney to the bladder and defines a lumen extending within. The first end portion is adapted to assume a retaining configuration when placed substantially within the kidney. The first end portion includes an interior space in communication with the lumen of the elongated portion and at least one opening in communication with the interior space for urine drainage from the kidney to the ureteral stent. The second end portion flares outward when placed substantially within the bladder to maintain position substantially within the bladder. The second end portion is collapsible to prevent fluid from passing into the lumen and causing patient discomfort.

Embodiments of this aspect of the invention can include the following features. In one embodiment, the second end portion includes a pleated segment including a plurality of folds at a wider part of the second end portion. The plurality of folds increase the bulk of the second end portion and facilitate retention of the second end portion substantially within the bladder. The pleated segment may be formed from a polymer, such as silicone or ethylene-vinyl acetate, or a polymer solution, such as a mixture of polyurethane and polycarbonate.

In another embodiment, the second end portion includes a plurality of inner segments and a plurality of outer segments. The second end portion is configured such that each one of the plurality of outer segments overlaps at least one of the plurality of inner segments. The plurality of inner and outer segments may be formed from a polymer or a polymer solution of polyurethane and polycarbonate. Additionally, the plurality of inner and outer segments may include a plurality of folds to increase the bulk of the second end portion, thereby facilitating retention of the second end portion within the bladder and facilitating prevention of urine from the bladder from entering the second end portion.

In yet another embodiment, the second end portion includes a plurality of segments, wherein each one of the plurality of segments is adjacent and overlapping at least one other segment of the plurality of segments. The plurality of segments may be formed from a polymer or a polymer solution, such as a polymer solution of polyurethane and polycarbonate. In some embodiments, the plurality of segments may include a plurality of folds to increase the bulk of the second end portion.

In another aspect, the invention relates to a ureteral stent. The ureteral stent, according to this aspect of the invention, includes an elongated portion, a first end portion extending from one end of the elongated portion, and a second end portion extending from another end of the elongated portion. The elongated portion has a length sufficient to extend substantially within the ureter from the kidney to the bladder and defines a lumen extending within. The first end portion is adapted to assume a retaining configuration when placed substantially within the kidney. The first end portion includes an interior space in communication with the lumen of the elongated portion and at least one opening in communication with the interior space for urine drainage from the kidney to the ureteral stent. The second end portion is wrapped to form a conical structure. The second end portion is adapted for placement and for maintaining position substantially within the bladder.

Embodiments of this aspect of the invention can include the following features. In one embodiment, the conical structure includes a first end, a second end including a width greater than a width of the first end, and a coiled segment disposed between the first and second ends. The coiled segment includes at least one and a half windings. In another embodiment, the second end portion is made from a biocompatible material, such as, for example, a polymer, a polymer solution of polyurethane and polycarbonate, or from a superelastic material, such as, a nickel-titanium alloy. In some embodiments, the second end portion includes a mesh to allow for drainage of urine from the second end portion. In another embodiment, the second end portion includes one or more tails for transporting liquid, such as, urine, to the bladder when the stent is placed within a patient.

In general, in another aspect, the invention features a method of inserting within a urinary system a ureteral stent, such as, one of the stents described above. The method includes inserting the stent into the urinary system of a patient and positioning the ureteral stent within the ureter such that the first end portion is within the kidney and the second end portion is within the bladder. The method may further include providing a catheter sized to receive the ureteral stent and using the catheter to insert and position the ureteral stent within the urinary system.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DESCRIPTION

Figure 1:
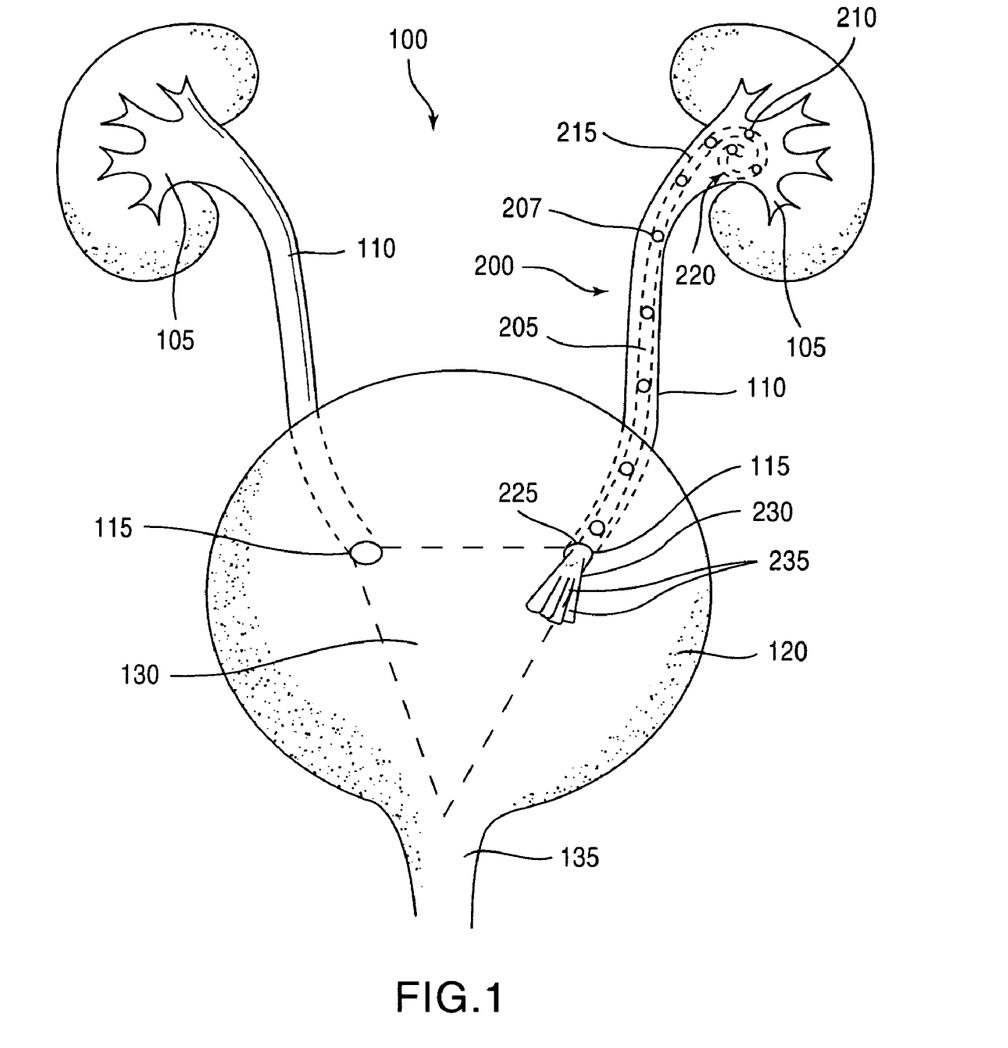
FIG. 1 is a schematic view of one embodiment of a stent according to the invention within a human urinary system.

Referring to FIG. 1, in a human urinary system 100, the ureters 110 transport urine from the kidneys 105 to the bladder 120. When one or both of the ureters 110 become blocked or obstructed due to, for example, the growth of a tumor or the entrapment of a kidney stone, a temporary alternative path is needed to provide fluid drainage between a patient's kidneys 105 and bladder 120. Ureteral stents are medical devices that are positioned within the ureters 110 to restore their patency and fluid drainage. Conventional ureteral stents have coiled or hooked ends adapted to retain the stent within the ureter 110. In the bladder 120, these end structures contact the bladder lining within a region of the bladder 120 known as the trigone 130.

The trigone 130 is located between the patient's uretheral opening 135 and two ureteral orifices 115. The trigone 130 contains a nerve bed and thus is a sensitive region of the bladder 120. Foreign objects, such as conventional stent end structures, placed within the trigone 130 stimulate the nerve bed causing the patient to experience bladder pain and irritation. The patient's discomfort arising from use of a convention ureteral stent may be increased if urine collects within the end structure in the bladder 120 and then is hydrostatically forced, due to pressure build up, to flow in a retrograde motion from the bladder 120 to the kidney 105.

The present invention concerns ureteral stents that reduce patient irritation and discomfort when placed within the ureter. The ureteral stents of the present invention include a bladder end structure that is positioned substantially within the bladder and is adapted to allow fluid, such as, urine, to flow through a lumen within the stent and into a patient's bladder. The bladder end structure flares outward when positioned in the bladder to prevent migration. To increase patient comfort, the stent's bladder end structure is collapsible in the absence of fluid flowing through the lumen to the bladder, thereby preventing retrograde motion of fluid from the bladder to the kidney. The bladder end structure may be made from a biocompatible material, such as, for example, a polymer (such as silicone, polyethylene terephthalate, tetrafluoroethylene, or ethylene-vinyl acetate) or a polymer solution (such as a mixture of polyurethane and polycarbonate).

Figure 2A:
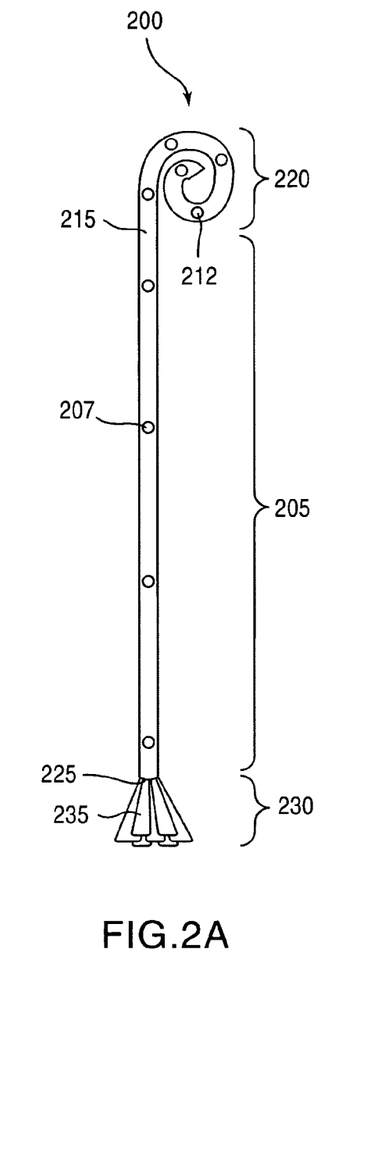
FIG. 2A is a side view of the stent of FIG. 1.
Figure 2B:
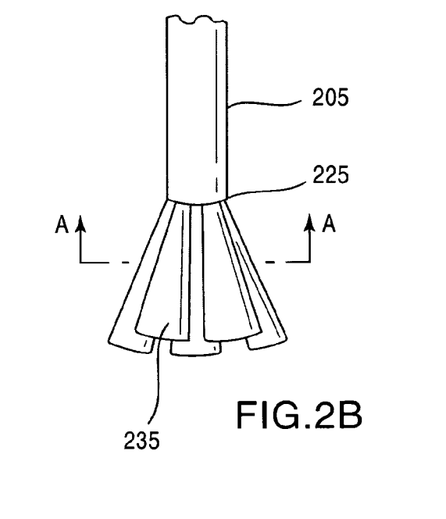
FIG. 2B is an enlarged side view of a proximal portion of the stent of FIG. 2A.

Referring to FIGS. 1 and 2A, a stent 200 according to the invention includes an elongated portion 205 that spans between a first and a second end portions 220, 230. The elongated portion 205 has a sufficient length to extend substantially the entire ureter 110 from the kidney 105 to the bladder 120. Within the elongated portion 205 is a lumen for transporting urine or other bodily fluids from the kidney 105 to the bladder 120. Located along the length of the elongated portion 205 can be a plurality of openings 207 in communication with the lumen. These openings are optional, and if present tend to increase drainage of urine through the stent 200 and into the bladder 120.

The first and second end portions 220, 230 extend from opposite ends of the elongated portion 205 and have shapes adapted to retain the ureteral stent 200 within the ureter. In the embodiment shown in FIG. 2A, the first end portion 220 extends from a distal end 215 of the elongated portion 205 and has a pigtail coil shape that can be temporarily straightened for insertion and recoiled once positioned within the kidney 105. Alternatively, in some embodiments, the first end portion 220 may have a hook shaped end to anchor and inhibit downward movement of the ureteral stent 200 from the kidney 105 towards the bladder 120. In either embodiment, within the first end portion 220 lies a lumen, which is in fluid communication with the lumen extending through the elongated portion 205. To allow fluid from the kidney to enter into the ureteral stent 200, the first end portion 220 has at least one opening 210 in communication with the lumen.

Figure 2C:
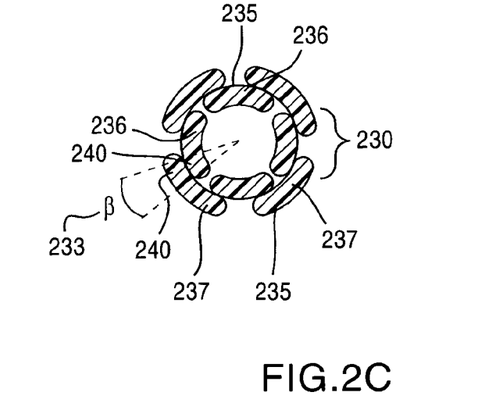
FIG. 2C is a cross-sectional view of the proximal portion of the stent of FIG. 2B in an open configuration, taken along line AA of FIG. 2B.
Figure 2D:
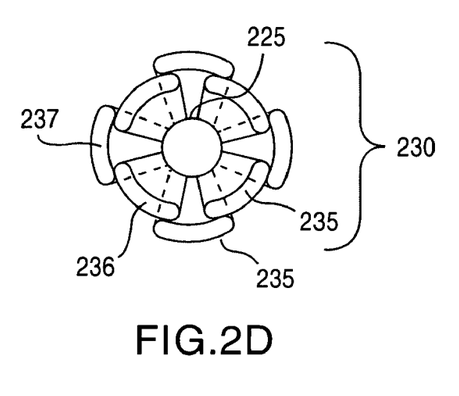
FIG. 2D is a bottom view of the proximal portion of the stent of FIG. 2B in the open configuration.

The second end portion 230 extends from a proximal end 225 of the elongated portion 205. The second end portion 230 anchors and prevents the upward motion of the ureteral stent 200. The second end portion 230 is a bulky, lightweight structure that has a large volume to weight ratio. The second end portion 230, as shown in FIGS. 2A-2D, has a plurality of segments 235, including a plurality of inner segments 236 and a plurality of outer segments 237. Each one of the plurality of outer segments 237 overlaps at least one of the plurality of inner segments 236 to form radially overlapping portions 240. FIG. 2C shows the radially overlapping portions 240 in this embodiment. A radial wedge labeled β 233 in FIG. 2C outlines a portion of the radial overlapping portions 240 of a representative inner segments 236 and in an adjacent outer segments 237. The inner and outer segment 236, 237 are made from a material that is soft and flexible, such as a biocompatible polymer or polymer solution. Examples of suitable polymers or polymer solutions are silicone, polyethylene terephthalate, tetrafluoroethylene, ethylene-vinyl acetate, and a mixture of polycarbonate and polyurethane. The segments 235 may be attached to the proximal end 225 of the elongated portion 205 by thermal bonding or adhesive.

Figure 2E:
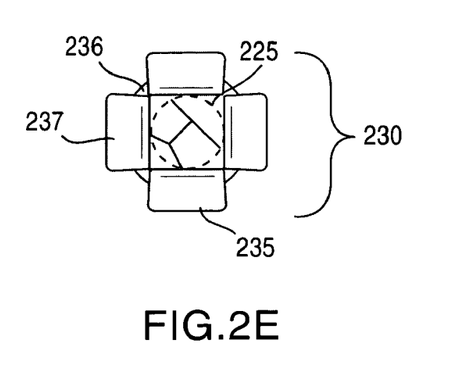
FIG. 2E is a bottom view of the proximal portion of the stent of FIG. 2B in a collapsed configuration.
Figure 2F:
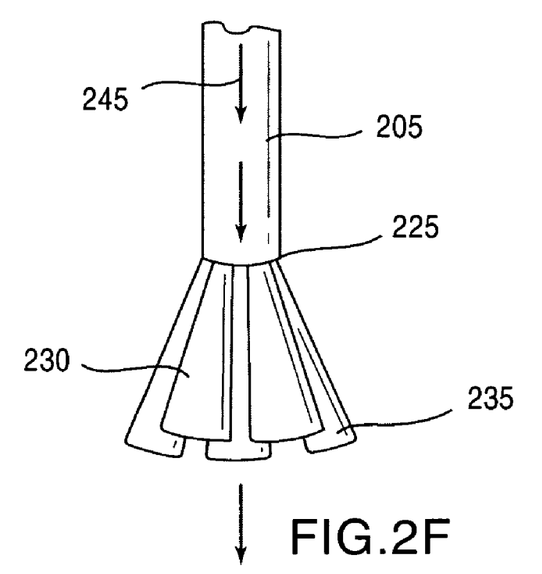
FIG. 2F is a schematic view of the proximal portion of the stent in the open configuration, allowing fluid to pass therethrough.
Figure 2G:
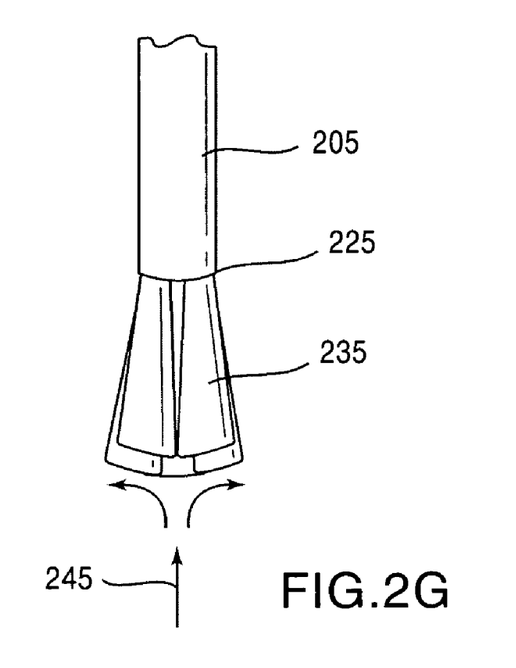
FIG. 2G is a schematic view of the proximal portion of the stent in the collapsed configuration, preventing fluid to flow into the proximal portion of the stent.

The segments 235 overlap creating a volume mass that will inhibit the ureteral stent 200 from migrating from the bladder 120. The overlapping portions 240 also inhibit fluid, such as urine, from returning into the elongated portion 205 once the fluid enters the bladder 120 by limiting fluid access to the lumen in the elongated portion 205. In the embodiment shown in FIGS. 2D-2E, the segments 235 are arranged in a concentric pattern extending outwards from the proximal end 225. The plurality of segments 235 are adapted to collapse in on themselves in the absence of fluid flowing from the elongated portion 205 through the second end portion 230. Referring to FIG. 2F, the segments 235, because of their flexibility and minimal weight, are pushed radially outward by the force of the flowing fluid 245 through the second end portion 230, thereby allowing the fluid to easily escape from the ureteral stent 200. Once the fluid has ceased flowing through the stent 200, the segments 235 collapse in on each other inhibiting fluid 245 from re-entering the ureteral stent 200, as shown in FIG. 2G.

Figure 2H:
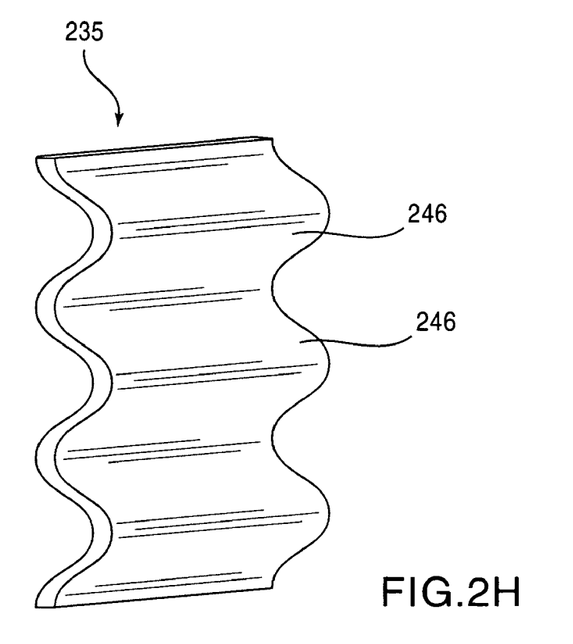
FIG. 2H is an enlarged prospective view of one embodiment of a segment of the proximal portion of a stent according to the invention.

Each of the segments 235 may be folded or waved, such that the segments 235 resemble seaweed, to increase the bulk of the second end portion 230 of the stent 200. FIG. 2H is a perspective view of a waved segment 235. Individual folds 246 not only increase the bulk of the second end portion 230, but also inhibit urine from entering into the lumen of the stent 200 when the second end portion 230 is collapsed. The folds 246 of the segments 235 overlap when the second end portion 230 is collapsed to cover an opening to the lumen proximate to the proximal end 225 of the elongated portion 205.

Figure 3A:
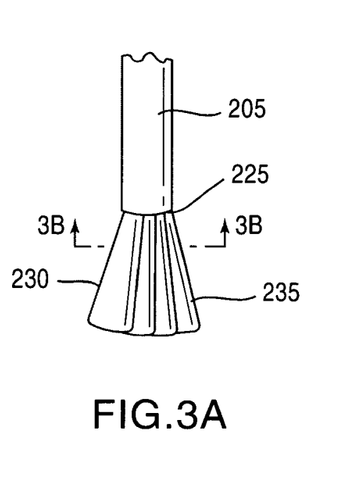
FIG. 3A is an enlarged side view of a proximal portion of another embodiment of a stent according to the invention.
Figure 3B:
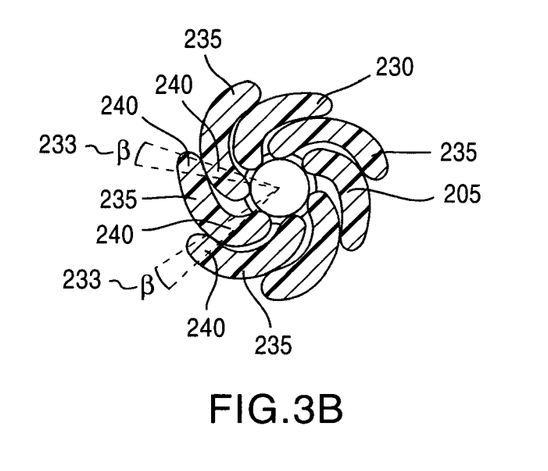
FIG. 3B is a cross-sectional view of the proximal portion of the stent of FIG. 3A in an open configuration, taken along line BB in FIG. 3A.

In another embodiment, the second end portion includes a plurality of segments 235. Each one of the plurality of segments 235 is adjacent and overlapping at least one other segment. The plurality of segments 235 are configured to provide bulk to the second end portion 230, such that the second end portion 230 is anchored within the bladder 120, thereby preventing distal migration of the stent 200. The plurality of segments 235 overlap to form radially overlapping portions 240 as outlined by radial wedges labeled β 233 in FIG. 3B.

Figure 3C:
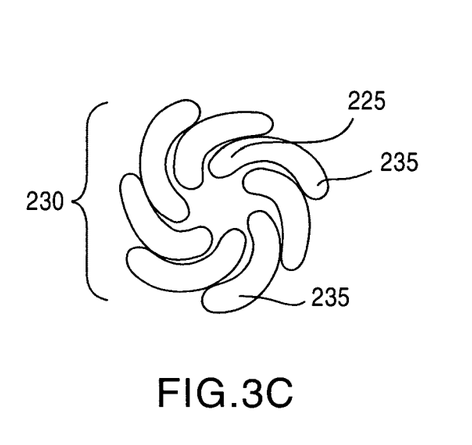
FIG. 3C is a bottom view of the proximal portion of the stent of FIG. 3A in an open configuration.
Figure 3D:
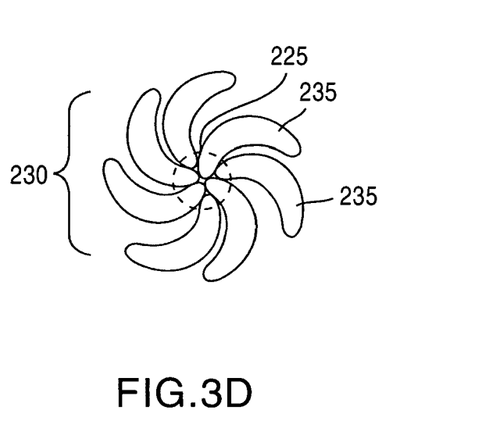
FIG. 3D is a bottom view of the proximal portion of the stent of FIG. 3A in a collapsed configuration.

Referring to FIGS. 3C-3D, the second end portion 230 has at least two different configurations. While the stent is actively draining fluids therethrough, the second end portion 230 is in an open configuration as shown in FIG. 3C. FIG. 3C shows a bottom view of the second end portion 230 of the stent 200 in the open configuration. As described above, fluid flowing under the influence of gravity forces the plurality of segments 235 to separate to allow passage of fluid therethrough. In the absence of flowing fluid, the plurality of segments 235 collapse in on themselves, as shown in FIG. 3D, thereby preventing fluid from entering the lumen of the stent at the proximal end 225.

Figure 4A:
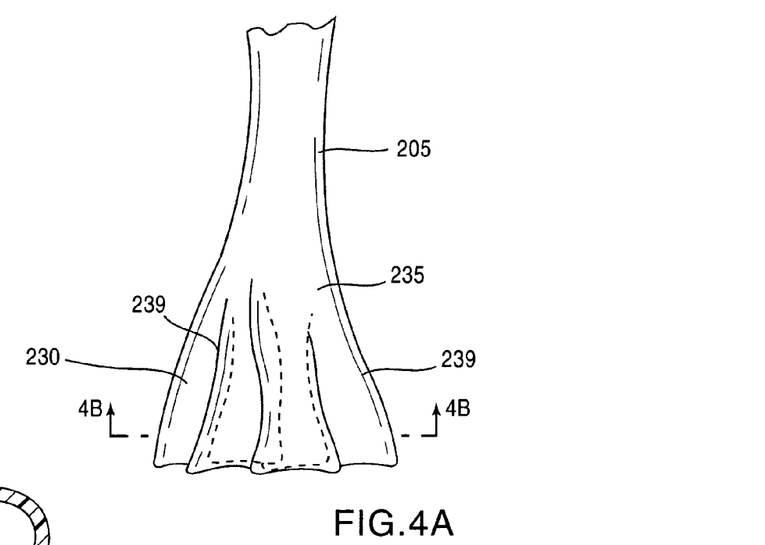
FIG. 4A is an enlarged side view of a proximal portion of another embodiment of a stent according to the invention.
Figure 4B:
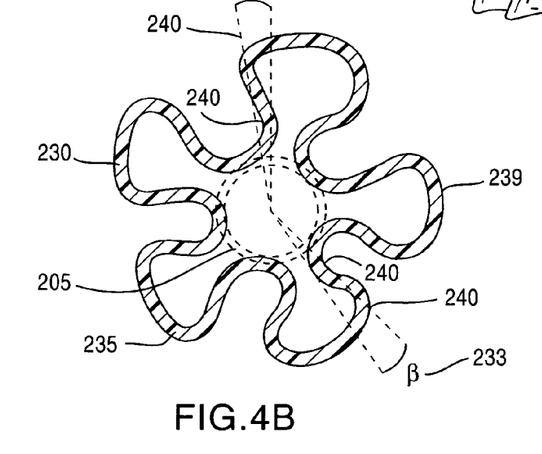
FIG. 4B is a cross-sectional view of the proximal portion of the stent of FIG. 4A in an open configuration, taken along line CC in FIG. 4A.
Figure 4C:
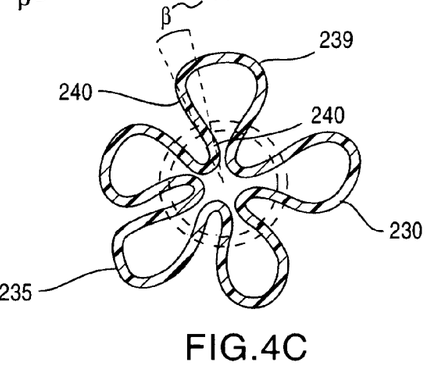
FIG. 4C is a cross-sectional view of the proximal portion of the stent of FIG. 4A in a collapsed configuration, taken along line CC in FIG. 4A.
Figure 5A:
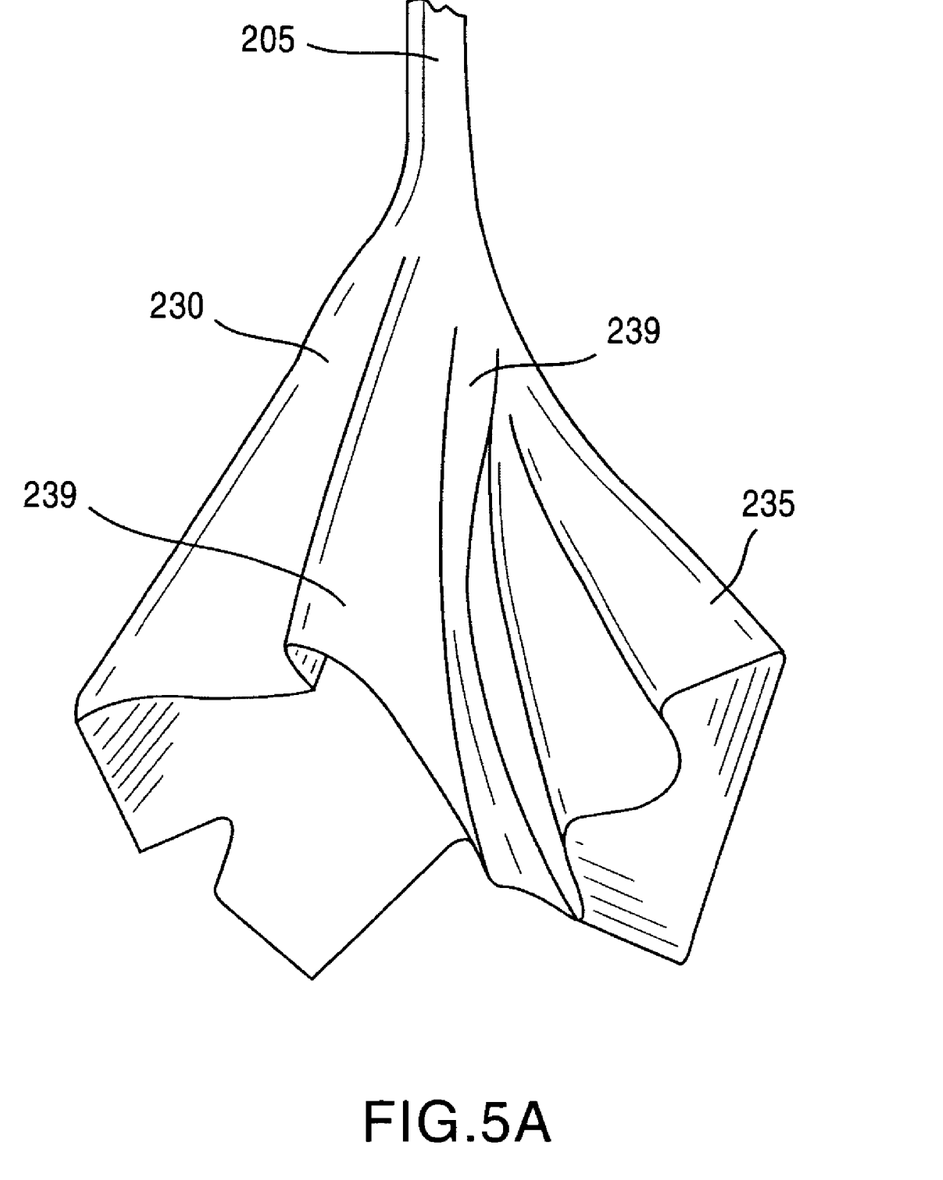
FIG. 5A is an enlarged side view of a proximal portion of another embodiment of a stent according to the invention in an open configuration.
Figure 5B:
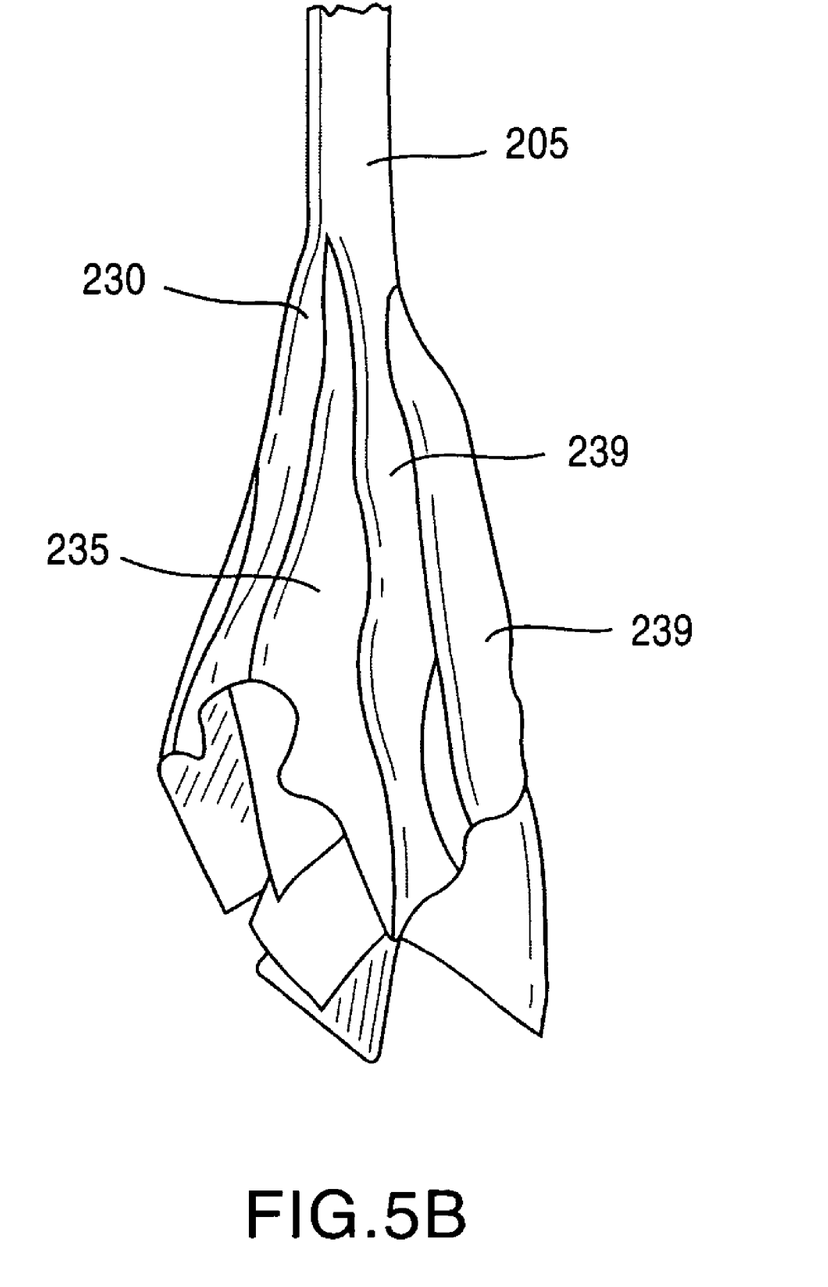
FIG. 5B is another enlarged side view of the proximal portion of the stent of FIG. 5A in a collapsed configuration.

In another embodiment shown in FIGS. 4A-4C, the second end portion 230 includes a single segment 235 made from a polymer such as silicone, polyethylene terephthalate, tetrafluoroethylene, or ethylene-vinyl acetate, or from a polymer solution of polycarbonate and polyurethane. The segment 235 folds over upon itself to form the radially overlapping portions 240. The radial wedges β 233 in FIGS. 4B-4C outline some of the radially overlapping portions 240 created by folds 239 in the segment 235. In FIGS. 4B and 4C, the folds 239 create a substantially regular pattern around the perimeter of the second end portion 230. FIGS. 4B and 4C show cross-sectional views of the second end portion 230 with a single segment 235 having a substantially regular folding pattern around its perimeter. FIG. 4B represents the second end portion 230 in an open fluid flow configuration and FIG. 4C represents the second end portion 235 in a closed configuration. Alternatively, the folds 239 in the second end portion 230 may form an irregular or non-distinct pattern around its perimeter, as shown in FIGS. 5A and 5B. FIG. 5A represents the second end portion 230 having a single segment 235 with an irregular folding pattern in the open configuration. FIG. 5B is an illustration of the second end portion 230 of FIG. 5A in the closed configuration. The folds 239 within the segment 235, through their volume, impede distal migration of the stent 200 from its position within the ureter. The folds 239 in the segment 235, when the second end portion 230 is collapsed, also prevent fluid from the bladder from entering the lumen of the elongated portion 205.

Figure 6A:
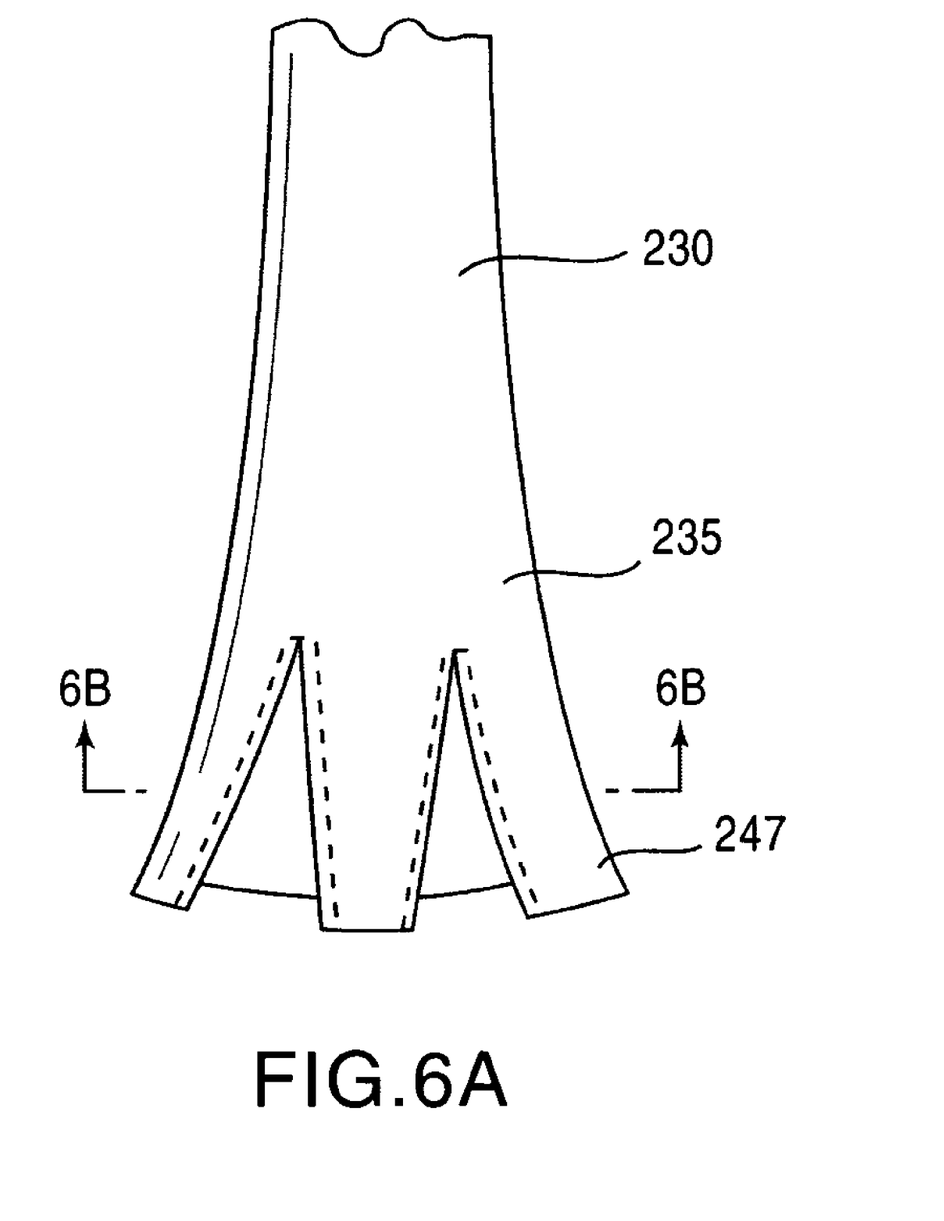
FIG. 6A is an enlarged side view of a proximal portion of another embodiment of a stent according to the invention.
Figure 6B:
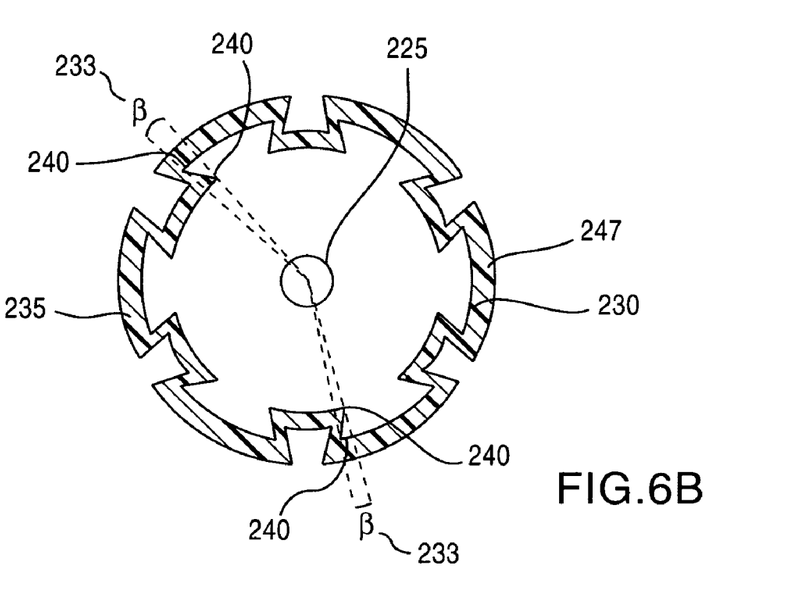
FIG. 6B is a cross-sectional view of the proximal portion of the stent of FIG. 6A in an open configuration, taken along line DD in FIG. 6A.
Figure 6C:
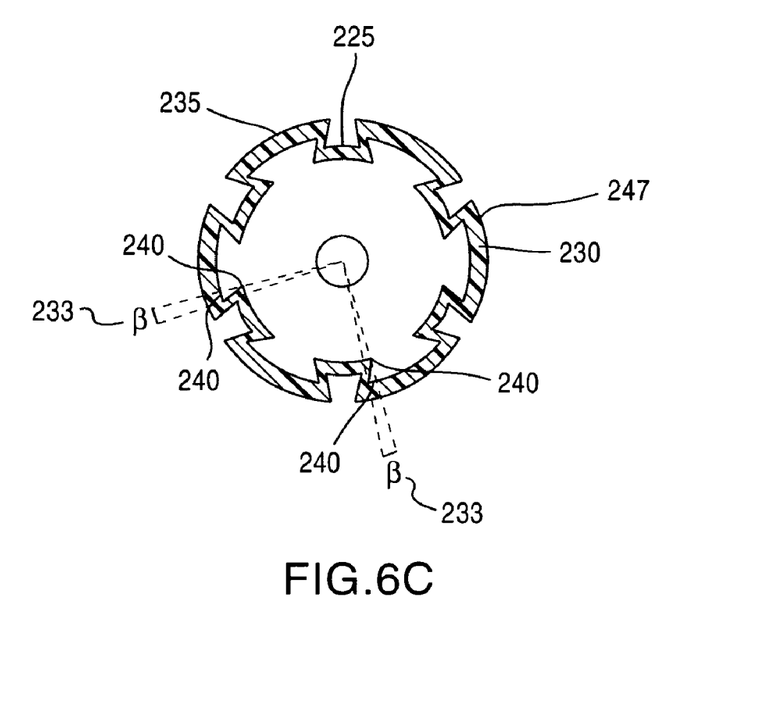
FIG. 6C is a cross-sectional view of the proximal portion of the stent of FIG. 6A in a collapsed configuration, taken along line DD in FIG. 6A.

In yet another embodiment shown in FIGS. 6A-6C, the second end portion 230 includes a segment 235 with pleats 247 at a wider part of the second end portion 230 to allow the segment 235 to temporarily expand, as shown in FIG. 6B, to drain the ureteral stent 200 during urination. The segment 235 is made from a polymer or a polymer solution and is soft and flexible such that the presence of the segment 235 within the bladder does not stimulate the trigone. The second end portion 230 will return to its original configuration as shown in FIG. 4C in the absence of fluid flow, and thereby limit fluid access from re-entering the lumen of the elongated portion 205. The pleats 247 in the segment 235 provide the second end portion 230 with a bulky configuration, which will prevent the second end portion 230 from migrating from its placed position within the bladder. The pleats 247 fold to create radially overlapping portions 240, a portion of which is outline by radial wedges β 233. The radially overlapping portions 240 add bulk to the second end portion 230, which facilitates distal migration prevention.

Figure 7A:
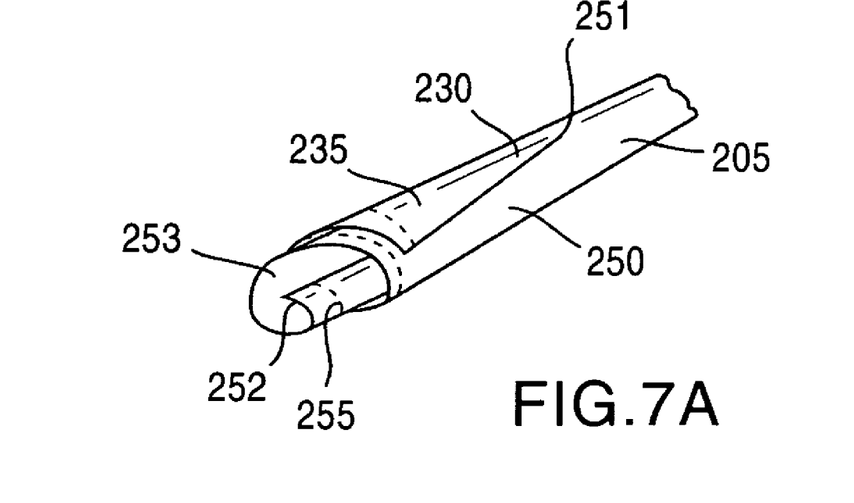
FIG. 7A is an enlarged perspective view of a proximal portion of another embodiment of a stent according to the invention in an inserted configuration.
Figure 7B:
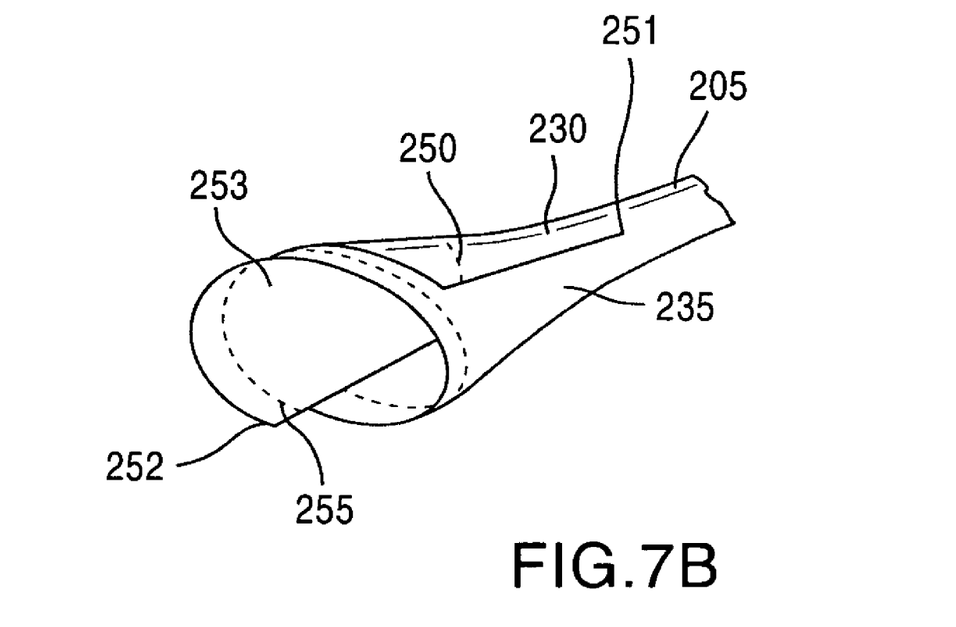
FIG. 7B is another enlarged perspective view of the proximal portion of the stent of FIG. 7A in an expanded configuration.

Referring to FIGS. 7A-7B, in another embodiment, the second end portion 230 is formed from a single segment 235 that is wrapped around itself, to form a conical structure 250 for maintaining position of the second end portion 230 substantially within the bladder 120. Embedded within the segment 235 may be a thin wire 255 of super-elastic material, such as a nickel-titanium alloy, that expands upon a phase change, thereby placing the second end portion 230 in an open configuration as shown in FIG. 7B. In a closed configuration, as shown in FIG. 7A, the second end portion 230 may be easily inserted and positioned within the body of a patient. The second end portion 230, shown in FIGS. 7A-7B, may be manufactured using the following procedure. First, the thin wire 255 is preformed to have a coil shape. Next, the thin wire 255 is temporarily straightened to be embedded within the segment 235. Preferably, the segment 235 is a thin (about 0.002 millimeters to 3 millimeters thick) rectangular, polymer sheet. Then, the thin wire 255 is placed along a diagonal of the segment 235 so that a corner of the rectangular sheet may be folded over the thin wire 255 enclosing the thin wire 255 within the segment 235. Next, the polymer segment 235 is heated to encase the thin wire 255 within the segment. Finally, the thin wire 255 is allowed to re-coil, thereby creating the conical structure 250 shown in FIGS. 7A-7B, which is then thermally bonded to the elongated portion 205 to produced the stent 200.

The conical structure 250 shown in FIGS. 7A-7B has a first end 251, a second end 252, and a coiled segment 253 disposed between the first and second ends 251, 252. The second end 252 has a width greater than the width of the first end 251 and by its width prevents distal migration of the second end portion 230 from the bladder 120 into the ureter 110. The coiled segment 253 includes at least one and a half windings forming the conical structure 250.

Figure 7C:
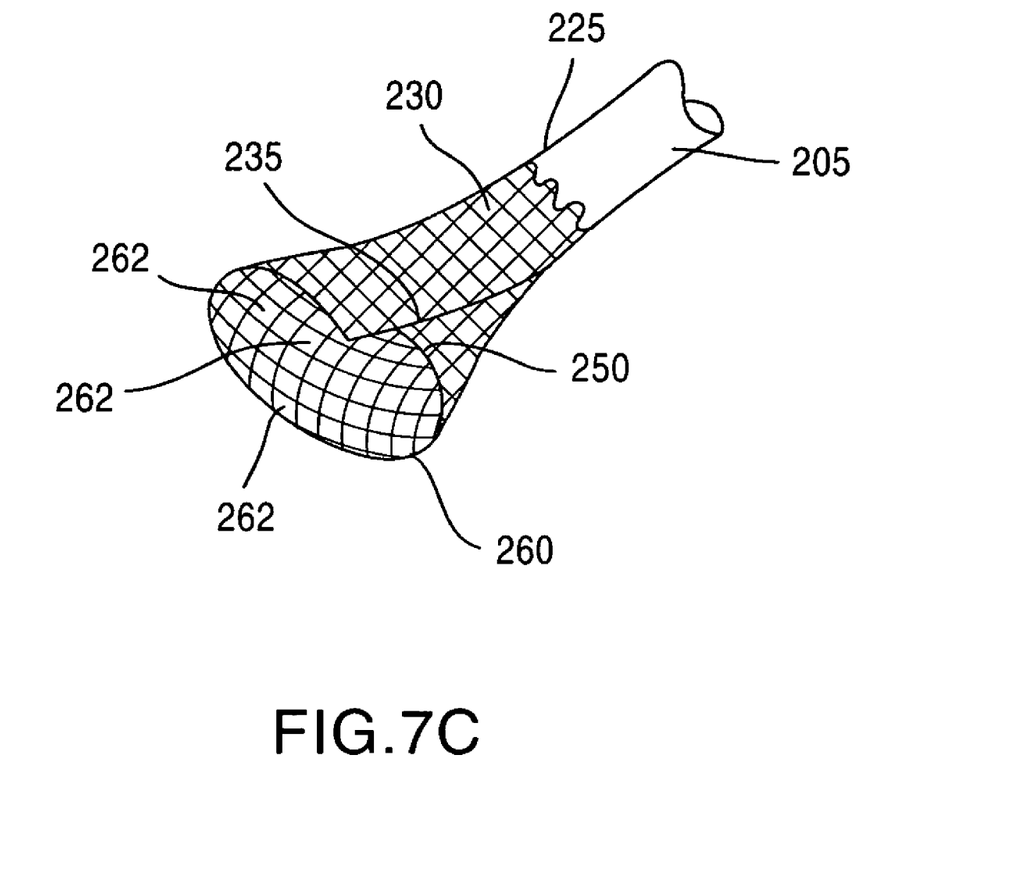
FIG. 7C is an enlarged perspective view of a proximal portion of another embodiment of a stent according to the invention.
Figure 7D:
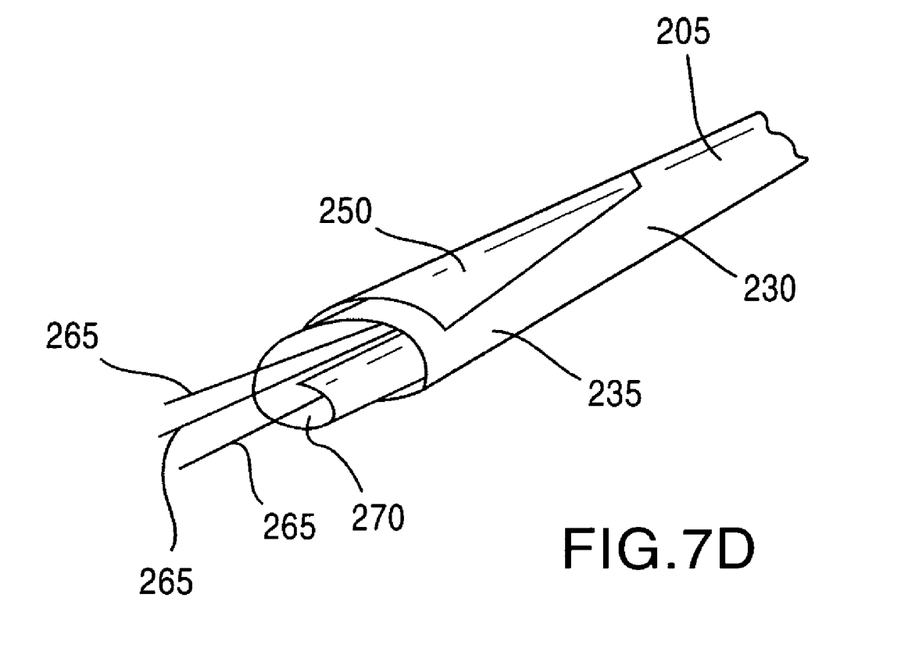
FIG. 7D is an enlarged perspective view of a proximal portion of another embodiment of a stent according to the invention.

Referring to FIG. 7C, in some embodiments to prevent a build up of urine within the second end portion 230, the segment 235 may include a mesh 260. The mesh 260 includes a plurality of openings 262 for the urine or other fluid to pass through, thereby preventing collection or build up of urine within the second end portion 230. In other embodiments, the ureteral stent 200 may further include one or more tails 265 extending from an inner surface 270 of the second end portion 230. The tails 265, as shown in FIG. 7D, transport liquid by capillary action through the second end portion 230 to the bladder 120. The tails 265 may be attached near the proximal end 225 of the elongated portion 205 or, alternatively, the tails 265 may be attached near the first end portion 220 and extend through the entire ureteral stent 200. The tails 265 provide a surface to transport fluid through the second end portion 230. In the embodiment shown in FIG. 7D, the tails 265 allow the second end portion 230 to remain in a substantially closed configuration during urination, thereby limiting urine from re-entering the lumen of the elongated portion 205 and preventing patient discomfort.

In operation, the ureteral stent 200 is inserted through a patient's urethra and advanced through the bladder 120 and ureter 110 to the kidney 105. Prior to insertion, the first end portion 220 is temporarily straightened and the second end portion 230 may be temporarily compressed for insertion into the patient's body.

The first end portion 220 may be straightened over a guide wire, which slides within the lumen of the ureteral stent 200 and is sufficiently stiff to hold the first end portion 220 in a straight configuration when inserting the ureteral stent 200. Alternatively, if other end structures other than a coil are used, such as hooks or malecots, these end structures are placed in an insertion configuration by for example, straightening the hooks or collapsing the malecots. Prior to insertion into the urinary system 100, the stent 200 may be disposed within a catheter or a cystoscope. The catheter or cystoscope compresses the second end portion 230 to facilitate insertion.

To position the ureteral stent 200 within the urinary system 100 of a patient, a medical professional, such as a physician inserts the guidewire into the patient's urethra and advances the guidewire until a distal end of the guidewire is located within one of the kidneys 105. After properly positioning the guidewire, the physician slides the catheter or cystoscope over the guidewire and then slides the ureteral stent 200 up over the guidewire, but within the lumen of the cystoscope. The physician may use a pusher to advance the ureteral stent 200 through the urinary system until the first end portion 220 is located within the kidney 105 and the second end portion 230 is within the bladder 120. Once positioned, the physician removes the catheter and guidewire from the patient's body, thereby allowing the first end portion 220 to re-coil and anchor itself within the kidney 105 and the second end portion 230 to maintain position within the bladder 120.

Variations, modifications, and other implementations of what is described herein will occur to those of ordinary skill in the art without departing from the spirit and scope of the invention. The invention is not to be limited only to the preceding illustrative description.

What is claimed is:

1. A ureteral stent, comprising:
   (a) an elongated portion defining a lumen extending therethrough and including a length sufficient to extend substantially within the ureter from the kidney to the bladder;
   (b) a first end portion extending from one end of the elongated portion, defining an interior space in communication with the lumen, and defining at least one opening in communication with the interior space, the first end portion for placement substantially within the kidney and adapted to assume a retaining configuration when placed substantially within the kidney; and
   (c) a second end portion extending from another end of the elongated portion and flaring outward when placed substantially within the bladder to maintain position substantially within the bladder, the second end portion including a single continuous sheet forming a conical wrapping, the conical wrapping being self-collapsible after implantation to at least partially prevent fluid from passing into the lumen from the bladder, the second end portion remaining proximal of the elongated portion when disposed within the bladder.

2. The ureteral stent of claim 1, wherein the second end portion includes a tail configured to transport liquid into the bladder.

3. A ureteral stent for facilitating drainage from the kidney to the bladder, the ureteral stent comprising:
   (a) an elongated portion defining a lumen extending therethrough and including a length sufficient to extend substantially within the ureter from the kidney to the bladder;
   (b) a first end portion extending from one end of the elongated portion, defining an interior space in communication with the lumen, and defining at least one opening in communication with the interior space, the first end portion for placement substantially within the kidney and adapted to assume a retaining configuration when placed substantially within the kidney; and
   (c) a second end portion extending from another end of the elongated portion and including a sheet wrapped such that a first side of the sheet is adjacent a second side of the sheet to form a conical structure, the second end portion adapted for placement, and for maintaining position, substantially within the bladder, the conical structure having a first end, a second end having a width greater than a width of the first end, and a wrapped segment disposed between the first and second ends, the wrapped segment including at least one and a half windings, the sheet defining a lumen configured to fluidically couple the lumen defined by the elongated portion with the bladder when in a first configuration, the sheet being self-collapsible into a second configuration such that the elongated portion is substantially fluidically isolated from the bladder when in the second configuration.

4. The stent according to claim 3 wherein the second end portion comprises a polymer.

5. The stent of claim 3 wherein the second end portion comprises one or more tails for transporting liquid into the bladder.

6. The ureteral stent of claim 3, wherein the second end portion is self-collapsible.

7. The ureteral stent of claim 3, wherein the second end portion is self-collapsible, the second end portion remaining proximal the elongated portion when disposed within the bladder.

8. The ureteral stent of claim 3, wherein the sheet is solid such that a liquid cannot pass through the sheet.

9. The stent of claim 3, wherein the second end portion comprises a super-elastic material.

10. The stent of claim 9, wherein the super elastic-material comprises a nickel-titanium alloy.

11. The stent of claim 3, wherein the second end portion comprises a mesh.

12. A ureteral stent comprising:
an elongated portion defining a lumen extending therethrough and including a length sufficient to extend substantially within the ureter from the kidney to the bladder;
a first end portion extending from one end of the elongated portion, the first end portion configured to be placed substantially within the kidney and adapted to assume a retaining configuration when placed substantially within the kidney; and
a second end portion extending from another end of the elongated portion, the second end portion including a single continuous sheet wrapped to form a conical structure, the conical structure being self-collapsible after implantation to at least partially prevent fluid from passing into the lumen of the elongated member from the bladder, the second end portion configured to be placed substantially within the bladder, the second end portion including a tail disposed within the conical structure and configured to transport liquid into the bladder.

13. The ureteral stent of claim 12, wherein the tail extends from an inner surface of the second end portion to a location beyond an end of the second end portion.

14. The ureteral stent of claim 12, wherein the tail is attached to the proximal end of the elongated member.

15. The ureteral stent of claim 12, wherein the tail is attached proximate to the first end portion of the elongated member such that a portion of the tail is disposed within the lumen of the elongated member.

16. The ureteral stent of claim 12, wherein the tail is configured to transport liquid by capillary action through the conical structure to the bladder.

17. The ureteral stent of claim 12, wherein the first end portion defines an interior space in communication with the lumen, the first end portion defines at least one opening in communication with the interior space.

18. The ureteral stent of claim 12, wherein the second end portion comprises a super-elastic material.

19. The ureteral stent of claim 18, wherein the super elastic-material comprises a nickel-titanium alloy.

20. The ureteral stent of claim 12, wherein the second end portion comprises a mesh.

* * * * *